(12) United States Patent
Bertrand et al.

(10) Patent No.: US 8,658,222 B2
(45) Date of Patent: Feb. 25, 2014

(54) TOPICAL COMPOSITION

(75) Inventors: Magali Bertrand, Haguenau (FR); Philippe Henriat, Chartres Cedex (FR)

(73) Assignee: Reckitt & Colman (Overseas) Limited, Slough, Berkshire (GB)

( * ) Notice: Subject to any disclaimer, the term of this patent is extended or adjusted under 35 U.S.C. 154(b) by 0 days.

(21) Appl. No.: 13/144,132

(22) PCT Filed: Jan. 15, 2010

(86) PCT No.: PCT/GB2010/000051
§ 371 (c)(1), (2), (4) Date: Aug. 21, 2011

(87) PCT Pub. No.: WO2010/082024
PCT Pub. Date: Jul. 22, 2010

(65) Prior Publication Data
US 2011/0311658 A1  Dec. 22, 2011

(30) Foreign Application Priority Data

Jan. 15, 2009  (GB) ................... 0900582.8

(51) Int. Cl.
*A01N 65/00*  (2009.01)

(52) U.S. Cl.
USPC .......................................... 424/725

(58) Field of Classification Search
None
See application file for complete search history.

(56) References Cited

U.S. PATENT DOCUMENTS

2012/0171294 A1 * 7/2012 Glenn et al. .................. 424/490

* cited by examiner

*Primary Examiner* — Michael Meller
(74) *Attorney, Agent, or Firm* — Ryan A. Schneider; Troutman Sanders LLP

(57) ABSTRACT

A topical composition comprising at least one active agent selected from a depilatory agent (s), an agent (s) for preventing or reducing the growth or re-growth of hair and an agent (s) for preventing or reducing in-growing hair, and a gas, wherein the at least one active agent and gas are dispersed in a cosmetically acceptable medium.

16 Claims, No Drawings

TOPICAL COMPOSITION

CROSS-REFERENCE TO RELATED APPLICATIONS

This application is a US National Stage of International Application No. PCT/GB2010/000051, filed 15 Jan. 2010, which claims the benefit of GB 0900582.8, filed 15 Jan. 2009.

FIELD OF THE INVENTION

The present invention relates to a topical composition comprising at least one active agent selected from a depilatory agent(s), an agent(s) for preventing or reducing the growth or re-growth of hair and an agent(s) for preventing or reducing in-growing hair. The present invention also relates to methods of using such compositions.

BACKGROUND OF THE INVENTION

Various topical compositions for treating the skin are known. Such compositions include depilatory compositions for removing unwanted hair. Typically, such depilatory compositions take the form of creams and include a depilatory active that degrades hair keratin. Once applied, the depilatory compositions are usually left on the skin to act for a predetermined period of time before being removed, for example, by rinsing with water.

To reduce the frequency of depilation, a composition for preventing or reducing the re-growth of hair may be applied in between depilation sessions. Like depilatory compositions, such compositions typically take the form of creams. However, such compositions are generally left to act on the skin and do not need to be removed after a predetermined period of time.

Frequent depilation or other forms of hair removal (e.g. shaving) may lead to an increased risk of in-growing hairs. This occurs when a hair curls back on itself and fails to reach the follicle opening. Sebum can build up around the hair shaft and cause a plug under the skin. This, in turn, can lead to inflammation and/or infection. Compositions for preventing or reducing in-growing hairs are also known. These tend to take the form of creams that are applied and left to act on the skin without the need for rinsing or removal.

BRIEF SUMMARY OF THE INVENTION

A new form of the above topical compositions has now been developed.

According to the present invention, there is provided a topical composition comprising
at least one active agent selected from a depilatory agent(s), an agent(s) for preventing or reducing the growth or re-growth of hair and an agent(s) for preventing or reducing in-growing hair, and
a gas,
wherein the at least one active agent and gas are dispersed in a cosmetically acceptable medium such that said topical composition is in the form of a foam prior to dispensing.

DETAILED DESCRIPTION OF PREFERRED EMBODIMENTS

In the composition of the present invention, the gas is incorporated such that it becomes entrapped and dispersed throughout the composition as a plurality of discrete bubbles. As a result, the composition takes the form of a mousse or foam and, advantageously, can be applied to the skin in a convenient manner.

It has been found that, by incorporating a gas into the composition, the weight of composition required to provide a certain level of efficacy, for example, in depilation, can be advantageously less than that which would be required using a comparable composition without the gas. This effect is surprising because the weight of active agent(s) present in the former is less than the weight of active agent(s) present in the latter.

It has also been found that, by incorporating a gas into the composition, the texture and/or skin-feel of the composition may be improved. The ease with which the composition may be applied may also be improved. Furthermore, the gas may not significantly effect on wetting properties of the composition.

Any suitable gas may be used in the composition. Examples include air, oxygen, nitrogen, hydrocarbon, carbon dioxide, fluorinated gases, oxides of nitrogen, noble gases and mixtures thereof. Suitable hydrocarbons include butane (e.g. n-butane and iso-butane) and propane. Suitable noble gases include helium, argon, neon, xenon and krypton. Suitable oxides of nitrogen include nitrogen monoxide and $N_2O$. In some embodiments of the present invention, it may be advantageous to avoid certain gases in the composition. Examples of such gases include hydrogen, methane, chlorine, fluorine, radon and ozone. Although oxygen and air may be used in many embodiments of the invention, it may be desirable to limit or avoid their use in compositions containing components that are sensitive to oxidation. Examples of such components include depilatory active agents, such as potassium thioglycolate, or active agents that can reduce or prevent hair growth or re-growth, such as resveratrol.

In a preferred embodiment, the gas comprises or is nitrogen.

Any suitable amount of gas may be employed. Preferably, the amount of gas is 1 to 30 volume % of the composition, more preferably 2 to 25 volume %, even more preferably 5 to 20 volume % of the composition. The amount of gas may be 0.0005 to 0.05 weight %, preferably 0.004 to 0.04 weight % of the composition.

The amount of gas may be selected to ensure that the desired level of efficacy may be maintained with a given volume of composition. The amount of gas should also be selected so as to ensure that the wetting behaviour of the composition is maintained at a desired level.

As mentioned above, the gas is incorporated in the composition such that it becomes entrapped and dispersed throughout the composition. The gas is preferably entrapped in the form of bubbles. The bubbles may have an average diameter of 1 nm to 5 mm, preferably 100 nm to 4 mm, more preferably 500 nm to 3 mm.

As mentioned above, the composition contains the gas and active agent(s) dispersed in a cosmetically acceptable medium. Such a medium may comprise water. Water may form at least 40 weight % of the composition. Preferably, the amount of water in the composition ranges from 50 to 98 weight %, more preferably 55 to 95 weight %. In one embodiment, the composition includes 80 to 95 weight % water. In another embodiment, the composition includes 50 to 60 weight % water and, in yet another embodiment, the composition includes 70 to 80 weight % water.

The composition may also include one or more emollients. Suitable emollients include oils, silicone oils, fatty alcohols, emollient esters, fatty acids and/or derivatives thereof. Where oil is used as an emollient, the oil may be a mineral oil, such as paraffinum liquidum, or a plant oil, such as sweet almond oil. Other suitable emollients include stearyl ethers, such as polypropylene glycol stearyl ether, polyethylene stearyl ether and polyoxyethylene stearyl ether. Specific examples of such emollients include PPG-15 stearyl ether, polyoxyethylene (2) stearyl ether and polyethylene stearyl ether. Further emollients may include, but are not limited to, cetyl alcohol, stearyl alcohol, triglyceride oils, oleyl alcohol, isopropyl laurate, polyethylene glycols, petroleum jelly, and esters such as myristyl myristate, myristyl lactate, isopropyl palmitate, isopropyl myristate, sodium lauroyl glutamate, cetyl esters, PEG-7 glyceryl cocoate, decyl cocoate, polyglyceryl-4-isostearate, isotridecyl isononanoate, $C_{12-15}$ alkyl benzoate, caprylic/capric triglyceride, pentaerythrityl tetraisostearate.

The total amount of emollient may be present in an amount of 0.01 to 15 weight %, preferably 0.05 to 7 weight % of the composition.

The composition may also include a humectant, such as glycerin. The humectant may be present in an amount of 0.01 to 5 weight % of the composition.

In a preferred embodiment, the composition includes a depilatory active. The depilatory active is a compound capable of degrading keratin and may be, for example, a sulphur compound such as potassium thioglycolate, dithioetythritol, thioglycerol, thioglycol, thioxanthine, thipsalicylcic acid, N-acetyl-L-cysteine, lipic acid, $NaHSO_3$, $Li_2S$, $Na_2S$, $K_2S$, $MgS$, $CaS$, $SrS$, $BaS$, $(NH_4)_2S$, sodium dihydrolipoate 6,8-dithiooctanoate, sodium 6,8-dithiooctanoate, salts of hydrogen sulphide for example NaSH or KSH, thioglycolic acid, thioglycerol, 2-mercaptopropionic acid, 3-mercaptopropionic acid, thiomalic acid, ammonium thioglycolate, glyceryl monothioglycolate, monoethanolamine thioglycolate, monoethanolamine, diammonium dithiodiglycolate, ammonium thiolactate, monoethanolamine thiolactate, thioglycolamide, homo-cysteine, cysteine, glutathione, dithiothreitol, dihydrolipoic acid, 1,3-dithiopropanol, thioglycolamide, glycerylmonothioglycolate, thioglycolhydrazine, keratinase, hydrazine sulphate, hydrazine disulphate triisocyanate, guanidine thioglycolate, calcium thioglycolate and/or cysteamine. However, the composition is preferably substantially or, more preferably, is completely free from depilatory agents that destroy the thermodynamic equilibrium or the surface tension of the composition; examples of such agents include alkali metal sulphides.

Preferred depilatory compounds are thioglycolates, or their precursor thioglycolic acid. Most preferred is potassium thioglycolate, which may be produced by mixing thioglycolic acid with a neutralising source of potassium hydroxide (as noted above excess potassium hydroxide over that required to effect neutralisation cannot be used).

The depilatory active may be present in an amount of 2 to 25 weight %, preferably 5 to 20 weight %, more preferably 10 to 15 weight %. In one embodiment, the composition includes potassium thioglycolate in an amount of 2 to 25 weight %, preferably 5 to 20 weight %, more preferably 10 to 15 weight %.

Where a depilatory active is used, the composition may desirably include an accelerator that will accelerate the hair removal reaction. Examples of such accelerators include urea, thiourea, dimethyl, isosorbide (DMI), ethoxydiglycol (Transcutol) or methyl propyl diol (MP diol). Preferably the accelerator is urea. The composition according to the invention preferably comprises from 5% to 15% wt, more preferably from 6 to 10 wt % of an accelerator (e.g. urea).

The composition of the present invention may comprise an agent(s) for preventing or reducing the growth or re-growth of hair. Preferably, the agent(s) for preventing or reducing the growth or re-growth of hair is resveratrol. The agent(s) for preventing or reducing the growth or re-growth of hair may be present in an amount of 0.05 to 5 weight % of the composition.

The composition of the present invention may comprise an agent(s) for preventing or reducing in-growing hair. Preferably, the agent(s) for preventing or reducing in-growing hair comprises glycolic acid. Where glycolic acid is used, it is preferably used in an amount of 1 to 10 weight %, more preferably 3 to 6 weight %.

Glycolic acid may be used in combination with at least one of allantoin, green tea extract and/or white grape skin extract. Such additives may help to reduce redness, irritation and/or act as a skin-conditioning agent. Where allantoin is used, it is preferably used in an amount of 0.05 to 5 weight %, more preferably 0.1 to 1 weight %. Where green tea extract is employed, it is preferably present in an amount of 0.1 to 5 weight %, more preferably 0.1 to 2 weight %. Where white grape skin extract is used, it is preferably used in an amount of 0.005 to 0.1 weight %, more preferably 0.01 to 0.05 weight %.

The composition of the present invention may optionally include one or more surfactant(s). The surfactant may be anionic, cationic or non-ionic. It is preferably non-ionic. Examples of suitable surfactants include cetearyl phosphate, cetearyl alcohol, cetearyl glucoside, cetostearyl alcohol and/or ceteareth 20. It is preferably present in an amount of from 0.5 to 15 wt % relative to the weight of the depilatory cream composition.

The composition may optionally include a source of alkalinity. In one embodiment, the composition includes a depilatory active and a source of alkalinity. The source of alkalinity may include hydroxides, such as hydroxides of alkali and alkaline earth metals. Suitable hydroxides include sodium hydroxide, potassium hydroxide, calcium hydroxide and magnesium hydroxide. Preferably, calcium hydroxide is employed, optionally together with potassium hydroxide. The source of alkalinity (e.g. calcium hydroxide) may be present in an amount of 0.1 to 10 weight %, preferably 1 to 6 weight %, for example 2 to 5 weight % of the composition.

The composition may comprise other optional ingredients, such as perfumes, preservatives, pigments and fillers. Chelating agents, such as sodium gluconate, may also be present. Where employed, the chelating agent may be present in an amount of less than 1 weight %, preferably 0.01 to 0.5 weight %, for example 0.05 to 0.1 weight %.

The composition may also include an additive that prevents phase separation. Suitable additives include polymers or copolymers of acrylic acid, for example, an acrylate copolymer. Such additives may be present in an amount of up to 2 weight %, preferably less than 1 weight %, more preferably less than 0.5 weight %, for example 0.1 to 0.4 weight %.

The composition may also include a malodour absorbent and/or adsorbent, such as spray dried silica. Such absorbents/adsorbents may desirably be present if the composition also includes a depilatory active agent. Such absorbents may be present in an amount of up to 2 weight %, preferably less than 1 weight %, and more preferably less than 0.5 weight %, for example 0.001 to 0.1 weight %.

Optionally, additives such as Aloe Vera and plant oils, such as sweet almond oil, may also be included in the composition. Such additives are employed in amounts of less than 1 weight %, for example, 0.1 to 0.5 weight % of the composition.

The composition is preferably an oil-in-water emulsion.

In one embodiment, the composition comprises:

a depilatory agent, such as potassium thioglycolate, optionally, an accelerator, such as urea, optionally, a source of alkalinity, such as potassium hydroxide, optionally, at least one emollient, a gas, such as nitrogen, and water, for example, in an amount of 55 to 65 weight %.

In another embodiment, the composition comprises:

an agent(s) for preventing or reducing the growth or re-growth of hair, such as resveratrol, optionally, an emollient, a gas, such as nitrogen, and water, for example, in an amount of 85 to 95 weight %.

In yet another embodiment, the composition comprises:

an agent(s) for preventing or reducing in-growing hair, such as glycolic acid, optionally, an emollient, a gas, such as nitrogen, and water, for example, in an amount of 70 to 80 weight %.

The composition may be contained in any suitable container, such an unpressurised container. The composition is contained in the container in the form of a mousse or foam. Accordingly, the composition is not an aerosol composition that exists in the form of a mousse or foam only upon release from a pressurised container.

According to a further aspect of the present invention, there is provided a method of depilation comprising:

applying a composition as discussed above and containing a depilatory active to the skin;

allowing the composition a residence time on the skin in order to degrade the hairs on the skin's surface;

at the end of the residence time removing the composition and depilated hairs from the skin; and rinsing the skin.

According to another aspect of the present invention, there is provided a method of preventing or reducing the growth or re-growth of hair, said method comprising applying, to the skin, a composition as discussed above and containing an active agent(s) for preventing or reducing the growth or re-growth of hair.

According to yet another aspect of the present invention, there is provided a method of preventing or reducing the in-growing of hair comprising applying, to the skin, a composition as discussed above and containing an active agent(s) for preventing or reducing the in-growing of hair.

For the purposes of the present invention the term 'foam' is intended to cover compositions in the form of liquids, gels, stabilised emulsions at standard room temperature and pressure which have a gas trapped therein as dispersed bubbles. For the avoidance of doubt the term 'foam' also covers mousses, aerated creams and aerated pastes.

These and other aspects of the present invention will now be described with respect to the following Examples.

Example 1

Depilatory compositions having the formulations set out in Table 1 below were produced.

TABLE 1

| | | Aerated formulae | | |
|---|---|---|---|---|
| RM Name | Standard formula % wt | 10% $N_2$ in volume % wt | 17% $N_2$ in volume % wt | 25% $N_2$ in volume % wt |
| Deionised Water | 59.61 | 58.603 | 58.597 | 58.588 |
| Cetearyl Alcohol 30/70 | 4.30 | 4.299 | 4.299 | 4.298 |
| Ceteareth-20 | 1.66 | 1.660 | 1.660 | 1.659 |
| Sweet Almond Oil | 0.10 | 0.100 | 0.100 | 0.100 |
| Glycerin | 1.20 | 1.200 | 1.200 | 1.200 |
| Calcium hydroxide | 3.70 | 3.700 | 3.699 | 3.699 |
| Sodium gluconate | 0.20 | 0.200 | 0.200 | 0.200 |
| Magnesium trisilicate | 0.35 | 0.350 | 0.350 | 0.350 |
| Urea 46% N | 7.70 | 7.699 | 7.698 | 7.697 |
| Acrylates copolymer | 0.11 | 0.110 | 0.110 | 0.110 |
| Spray dried silica | 0.04 | 0.040 | 0.040 | 0.040 |
| Potassium thioglycolate | 13.10 | 13.098 | 13.097 | 13.095 |
| Potassium Hydroxide Solution | 1.10 | 1.100 | 1.100 | 1.100 |
| Thick Mineral Oil | 4.70 | 4.699 | 4.699 | 4.698 |
| Inorganic Silica/Silicate | 0.20 | 0.200 | 0.200 | 0.200 |
| Cosmetic Talc | 1.80 | 1.800 | 1.800 | 1.799 |
| Fragrance (Thelma 200) | 0.50 | 0.500 | 0.500 | 0.500 |
| Lotus flower milk | 0.13 | 0.130 | 0.130 | 0.130 |
| Colouring (Pink Paste-$TiO_2$, pink dye & propylene glycol) | 0.50 | 0.500 | 0.500 | 0.500 |
| nitrogen | 0.00 | 0.012 | 0.023 | 0.037 |
| | 100.00 | 100.000 | 100.000 | 100.000 |

The composition was made in the following way.

The components of the composition were blended using standard procedures for making a depilatory composition. These are known to the man skilled in the art. Thereafter, the resulting composition is subjected to aeration using an aerating machine. The parameters of the aerating machine can be adjusted depending on the properties required for a particular composition.

The compositions were tested by a panel of fifteen volunteers. All panellists found the compositions to be effective, moisturising and easy-to-spread. They also liked the appearance, texture and skin-feel of the compositions. However, it was found that the same level of efficacy with respect to depilation could be achieved using lower weight amounts of the gas-containing compositions.

Example 2

Depilatory compositions having the formulations set out in Table 2 below were produced. These embodiments can be made in the same manner as those of Example 1.

TABLE 2

| | | Aerated formulae | | |
|---|---|---|---|---|
| Raw material | Standard formula % in weight | 10% $N_2$ in volume % in weight | 17% $N_2$ in volume % in weight | 25% $N_2$ in volume % in weight |
| cet alcohol | 7.700 | 7.699 | 7.698 | 7.697 |
| cet-20 | 3.000 | 3.000 | 2.999 | 2.999 |
| arlamol | 2.200 | 2.200 | 2.199 | 2.199 |
| PE | 2.200 | 2.200 | 2.199 | 2.199 |

TABLE 2-continued

| Raw material | Standard formula % in weight | Aerated formulae | | |
|---|---|---|---|---|
| | | 10% N₂ in volume % in weight | 17% N₂ in volume % in weight | 25% N₂ in volume % in weight |
| Ca OH2 | 3.900 | 3.900 | 3.899 | 3.899 |
| Na gluconate | 0.100 | 0.100 | 0.100 | 0.100 |
| Mg trisilicate | 0.400 | 0.400 | 0.400 | 0.400 |
| pink paste | 0.500 | 0.500 | 0.500 | 0.500 |
| urea | 7.800 | 7.799 | 7.798 | 7.797 |
| lotus milk | 0.150 | 0.150 | 0.150 | 0.150 |
| acrylat | 0.120 | 0.120 | 0.120 | 0.120 |
| thelma silica | 0.530 | 0.530 | 0.530 | 0.530 |
| | 0.030 | 0.030 | 0.030 | 0.030 |
| TGK | 12.800 | 12.798 | 12.797 | 12.795 |
| KOH | 0.970 | 0.970 | 0.970 | 0.970 |
| water | 57.600 | 57.593 | 57.587 | 57.579 |
| nitrogen | 0.000 | 0.012 | 0.023 | 0.037 |
| | 100.000 | 100.000 | 100.000 | 100.000 |

Example 3

Compositions for preventing or reducing the re-growth of hair having the formulations set out in Table 3 below were produced. These embodiments can be made in the same manner as those of Example 1.

TABLE 3

| Ingredient | Standard formula % in wt | Aerated formula, 10% N₂ in volume % in wt |
|---|---|---|
| Arlamol E | 1.9 | 1.900 |
| Cetyl Alcohol | 0.5 | 0.450 |
| Brij 721 | 1.8 | 1.800 |
| Brij 72 | 1.1 | 1.100 |
| White paste | 0.3 | 0.320 |
| Deionised water | 90.5 | 90.528 |
| Na4 EDTA | 0.1 | 0.110 |
| Ethanol 96% | 1.2 | 1.200 |
| Eldew SL-205 | 0.9 | 0.900 |
| Resveratrol | 0.1 | 0.110 |
| Cocosoft D | 0.1 | 0.100 |
| Aloe Vera | 0.1 | 0.120 |
| Phenonip | 1.0 | 1.000 |
| Synthalen K (Carbomer 940) | 0.4 | 0.350 |
| Nitrogen | 0.0 | 0.013 |
| | 100.0 | 100.000 |

Example 4

Compositions for preventing or reducing the occurrence of in-growing hairs having the formulations set out in Table 4 below were produced. These embodiments can be made in the same manner as those of Example 1.

TABLE 4

| | Standard formulation | Aerated | |
|---|---|---|---|
| | | 13% N₂ in volume (% w/w) | 22% N₂ in volume (% w/w) |
| Raw material | 8.35 | 8.349 | 8.347 |
| cetearyl alcohol | 2.80 | 2.800 | 2.799 |
| ceteareth20 | 0.55 | 0.550 | 0.550 |

TABLE 4-continued

| | Standard formulation | Aerated | |
|---|---|---|---|
| | | 13% N₂ in volume (% w/w) | 22% N₂ in volume (% w/w) |
| PPG 15 stearyl ether | 0.10 | 0.100 | 0.100 |
| sweet almond oil | 0.15 | 0.150 | 0.150 |
| light mineral oil | 0.15 | 0.150 | 0.150 |
| BHT | 0.40 | 0.400 | 0.400 |
| PMX depil white paste | 75.53 | 75.517 | 75.506 |
| deionised water | 0.11 | 0.110 | 0.110 |
| Na4 EDTA P | 0.18 | 0.180 | 0.180 |
| Allantoin | 5.40 | 5.399 | 5.398 |
| glycolic acid 70% | 4.30 | 4.299 | 4.299 |
| KOH 50% | 1.00 | 1.000 | 1.000 |
| phenoxyethanol | 0.25 | 0.250 | 0.250 |
| camille 21 | 0.70 | 0.700 | 0.700 |
| veg ext herba green tea | 0.03 | 0.030 | 0.030 |
| white grapeskin extract | 8.35 | 8.349 | 8.347 |
| nitrogen | 0.00 | 0.017 | 0.032 |
| | 100.00 | 100.000 | 100.000 |

The invention claimed is:

1. A topical composition for removing unwanted hair, reducing growth or re-growth of hair consisting essentially of therapeutically effective amounts of cetearyl alcohol, sweet almond oil, glycerin, urea, potassium thioglycolate, and lotus flower milk.

2. The topical composition of claim 1, wherein the topical composition is in the form of a foam prior to dispensing from a container.

3. The topical composition of claim 1, wherein cetearyl alcohol is present in an amount of from 0.5 to 15 wt % relative to the weight of the topical composition.

4. The topical composition of claim 1, wherein sweet almond oil is present in an amount of from 0.01 to 15 wt % relative to the weight of the topical composition.

5. The topical composition of claim 1, wherein sweet almond oil is present in an amount of from 0.05 to 7 wt % relative to the weight of the topical composition.

6. The topical composition of claim 1, wherein glycerin is present in an amount of from 0.01 to 5 wt % relative to the weight of the topical composition.

7. The topical composition of claim 1, wherein urea is present in an amount of from 5 to 15 wt % relative to the weight of the topical composition.

8. The topical composition of claim 1, wherein urea is present in an amount of from 6 to 10 wt % relative to the weight of the topical composition.

9. The topical composition of claim 1, wherein potassium thioglycolate is present in an amount of from 2 to 25 wt % relative to the weight of the topical composition.

10. The topical composition of claim 1, wherein potassium thioglycolate is present in an amount of from 5 to 20 wt % relative to the weight of the topical composition.

11. The topical composition of claim 1, wherein potassium thioglycolate is present in an amount of from 10 to 15 wt % relative to the weight of the topical composition.

12. A topical foam composition for removing unwanted hair reducing growth or re-growth of hair consisting essentially of therapeutically effective amounts of sweet almond oil and lotus milk, wherein the topical composition is in the form of a foam prior to dispensing from a container.

13. The topical foam composition of claim 12, wherein sweet almond oil is present in an amount of from 0.01 to 15 wt % relative to the weight of the topical foam composition.

14. The topical foam composition of claim 12, wherein sweet almond oil is present in an amount of from 0.05 to 7 wt % relative to the weight of the topical foam composition.

15. A method of removing unwanted hair, reducing growth or re-growth of hair consisting essentially of applying the topical composition of claim 1.

16. A method of removing unwanted hair or reducing growth or re-growth of hair consisting essentially of applying the topical foam composition of claim 12.

* * * * *